(12) United States Patent
Dao

(10) Patent No.: US 8,679,045 B2
(45) Date of Patent: Mar. 25, 2014

(54) SUPINATING ARM AND ELBOW BRACE

(76) Inventor: Leland Henry Dao, Haleiwa, HI (US)

( * ) Notice: Subject to any disclaimer, the term of this patent is extended or adjusted under 35 U.S.C. 154(b) by 0 days.

(21) Appl. No.: 13/315,310

(22) Filed: Dec. 9, 2011

(65) Prior Publication Data

US 2012/0215146 A1    Aug. 23, 2012

Related U.S. Application Data

(60) Provisional application No. 61/459,290, filed on Dec. 9, 2010.

(51) Int. Cl.
*A61F 5/00* (2006.01)

(52) U.S. Cl.
USPC ............... 602/20; 602/21; 602/22; 602/75

(58) Field of Classification Search
USPC .............. 602/20–22, 60–62, 75–79; 128/878–879; 482/47, 124–125; 473/450
See application file for complete search history.

(56) References Cited

U.S. PATENT DOCUMENTS

| | | | |
|---|---|---|---|
| 4,191,373 A | | 3/1980 | Lancellotti |
| 4,632,105 A | * | 12/1986 | Barlow ............... 602/64 |
| 4,763,901 A | | 8/1988 | Richter |
| 5,228,682 A | * | 7/1993 | Wolf ............... 473/450 |
| 6,224,564 B1 | | 5/2001 | Korobow |
| 6,740,051 B2 | | 5/2004 | Hepburn et al. |
| 6,783,507 B1 | * | 8/2004 | Fisher ............... 602/22 |
| 6,866,646 B2 | | 3/2005 | Hopkins et al. |
| 7,442,133 B2 | * | 10/2008 | Wolf ............... 473/450 |
| 2006/0258965 A1 | | 11/2006 | Lee et al. |

* cited by examiner

*Primary Examiner* — Michael A. Brown

(74) *Attorney, Agent, or Firm* — St. Onge Steward Johnston & Reens LLC

(57) ABSTRACT

An arm brace including an extendable band, such as an elastic strap, that forms a supinating tension band. The distal end the band has a looped section for a user's wrist or finger for anchoring the brace, and the proximal end has a fastening device, such as a hook and loop fastener, for securing the proximal end to another portion of band after the band is wrapped around the forearm and stretched around the elbow and back towards the forearm. The extended band exerts a force that causes supination of the arm. In some embodiments, the inner surface of the proximal end of the band attaches to the outer surface of the band, and the looped section has a loop that closes at a notched section of the band, to provide proper comfort and positioning.

19 Claims, 5 Drawing Sheets

SUPINATING ARM AND ELBOW BRACE

FIELD OF THE INVENTION

This device pertains to arm braces which aid in the condition known as lateral epicondylar tendinopathy, or more commonly known as 'tennis elbow'. This is generally accepted as an injury to one of the forearm extensor muscle tendons such as the extensor carpi radialis brevis muscle which attaches to the bony prominence known as the lateral epicondyle.

BACKGROUND OF THE INVENTION

Lateral epicondylitis affects 1-2 percent of the population. The etiology is felt to be from repetitive overuse of the muscles originating on the lateral epicondyle. Previous braces have tried to immobize the forearm muscles, or hold the wrist in dorsiflexion alone.

Various treatment including epicondylar bandages and neutral position or counterforce extensor forearm braces have been tried, such as those of U.S. Pat. No. 6,224,564 to Korobow, U.S. Pat. No. 4,763,901 to Richter, and U.S. Pat. No. 4,191,373 to Lancellotti, but provide minimal relief.

SUMMARY OF THE INVENTION

In order to overcome the deficiencies of the prior art and to achieve at least some of the benefits discussed herein, the invention comprises an arm brace for rehabilitating an arm of a person, including a band for wrapping around an arm, the band having a distal end and a proximal end, a looped section at the distal end of the band for accommodating a portion of a hand/wrist of the arm to anchor the band thereto, wherein the band is extendable to an extended position, such that the band exerts a force that causes supination of the arm when the looped section is anchored to the hand/wrist, and a fastener at the proximal end of the band for securing the proximal end of the band to another portion of the band when the band is in the extended position, wherein the looped section of the band has a loop that closes at a notched section of the band, such that the looped portion has angled openings for accommodating a digit of the hand.

In some embodiments, the band is elastic. In certain embodiments, the fastener releasably attaches the proximal end to the band. In some cases, the band comprises an inner surface for contacting the arm and an outer surface, and the fastener comprises a hook and loop fastener, wherein the inner surface of the proximal end of the band fastens to the outer surface of the band. In some embodiments, the looped section is a fixed loop. In certain embodiments, the distal end of the band includes a second fastener, and the looped section at the distal end of the band is formed by a portion of the band secured to itself via the second fastener. In certain embodiments, the second fastener releasably attaches the distal end to the band. In some cases, the band comprises an inner surface for contacting the arm and an outer surface, and the fastener comprises a hook and loop fastener, wherein the outer surface of the proximal end of the band fastens to the inner surface of the band.

In other embodiments, the invention comprises a method of rehabilitating an arm of a person with an arm brace, including anchoring an extendable band to an arm by positioning a portion of a hand/wrist of the arm in a looped section located at the distal end of the band, extending the band around the arm such that it exerts a force that causes supination of the arm, and fastening a proximal end of the band to another portion of the band to secure the band in an extended position.

In some of these embodiments, the band is elastic. In certain embodiments, the step of fastening the proximal end of the band to another portion of the band comprises fastening the inner surface of the proximal end of the band to the outer surface of the band. In some cases, the step of anchoring comprises wrapping a distal section of the band around a wrist and fastening the distal end to the band to form the looped section. In certain cases, the step of extending the band around the arm comprises wrapping the band at least partially around a forearm in a spiral direction, pulling a proximal end of the strap to a lateral side of an elbow, pulling the proximal end past the elbow and around an upper arm, and pulling the proximal end back towards the forearm. In some embodiments, the step of anchoring comprises inserting at least one digit of a hand into a fixed loop. In some embodiments, the step of extending the band around the arm comprises passing the band over the back of the hand, wrapping the band at least partially around a wrist and forearm in a spiral direction, pulling the proximal end of the band to a lateral side of the elbow, pulling the proximal end past the elbow and around an upper arm, and pulling the proximal end back towards the forearm. In some cases, the looped section of the band has a loop that closes at a notched section of the band, such that the looped portion has angled openings for accommodating the digit of the hand. In certain cases, the step of anchoring comprises inserting a thumb into a fixed loop. In some embodiments, the method further comprises the step of increasing the force exerted on the arm by stretching the band to increase the length of the band. In some embodiments, the method comprises the step of decreasing the force exerted on the arm by relaxing the band to decrease the length of the band.

DETAILED DESCRIPTION OF THE INVENTION

Figure 1:
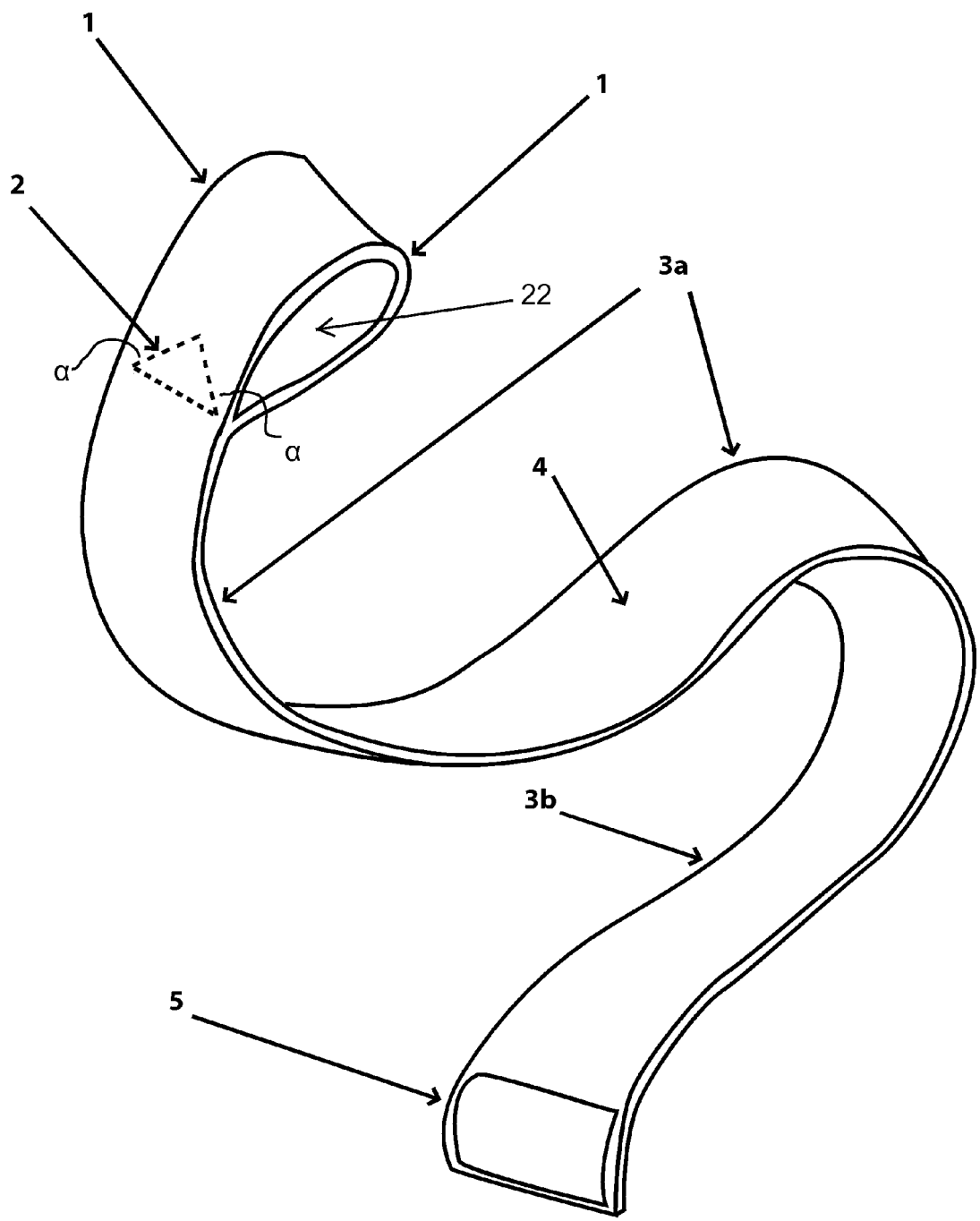
FIG. 1 is a perspective view of an arm brace in accordance with the invention.

The device comprises of a strap or brace, with an outer and inner surface, a notched looped leading end forming double or two openings, a supinating tension band section with inner and outer surface containing elastic properties, a fastening section on the outer surface of the body of the device, and an inner surface with a corresponding elastic fastening terminal end.

Another embodiment of the device comprises a strap or brace, with an outer and inner surface, having a fastening section on the proximal end, a supinating tension band or length section with inner and outer surface containing elastic properties, a fastening section on the outer surface of the body of the device, and an inner surface with a corresponding elastic fastening terminal end.

The elastic material found on the supinating tension band portion of the brace creates a springlike retractable tension force when secured on the user's arm. The proximal and distal ends of the brace secure the supinating tension band, encouraging a supination position of the forearm.

The proximal and distal ends of the brace may have a number of different anchoring or securing configurations to hold the central supinating tension band. Several configurations are described here. A brace with a looped end, containing two angled or notched openings for either the left or right thumb or other digit, which anchors, and initiates the supination and dorsiflexion position of the user's arm. This is worn by placing the user's thumb or anchoring digit into the corresponding notched loop, then wrapping the brace onto the back of the hand in a spiral direction, thereby pulling the hand in an externally rotated, or supinated position with a slight dorsiflexion of the wrist. The supinating tension band then wraps around the forearm in a spiral direction proximally onto the anterior surface of the forearm toward the lateral epicondyle of the elbow.

The supinating tension band is further wrapped behind the partially flexed lateral side of the elbow, then brought behind the distal part of the upper arm posteriorly above the elbow back towards the forearm. The supinating tension band is then wrapped onto itself on the forearm in a spiral manner, and wrapped once more around the proximal forearm, with the fastener attaching on the outer surface of the body of the device to the terminal end's inner surface with a means such as a velcro fastener. The spring like elasticity of the supinating tension band acts to oppose the forearm pronator muscles, thereby relaxing on the supinator and extensor muscles of the forearm.

Another embodiment of this bracing device shows a securing method of the distal end in which the continuous supinating tension band is secured to the wrist with a wrapping and fastening method using velcro or other fastening means to create a supinating wrist anchor for securing the supinating tension band distally.

Another embodiment of this bracing device shows a securing method of the distal end in which the noncontinuous central supinating tension band is secured to the wrist with an attached wrist cuff. A proximal arm or forearm cuff may also be used to secure the supinating tension band proximally to the arm.

The device utilizes the supinating tension band portion's elasticity to encourage the user's arm position in both supination and extension or dorsiflexion to alleviate forces affecting the extensor tendons such as the extensor carpi radialis brevis muscle which originates from the lateral epicondyle.

Although the elastic properties of the device does allow the hand to move to a pronated position, it reduces the full muscle and tendon lengthening, thereby reducing opposing tendon forces on the lateral epicondyle. This elastic force also encourages a passive supination and dorsiflexion, thereby further inhibiting active tendon tension. When the user's elbow is extended, the band creates a supinated and partially dorsiflexed forearm, a position ideal for the relief of lateral epicondylitis, or tennis elbow.

FIG. 1 shows one configuration comprising of a supinating arm and elbow brace with one end containing a double loop 1, notch section 2 with angle α forming angled openings 22 on either side of the loop 1, elastic supinating tension band portion with outer surface 3a with fastening attachments on the outer surface 4, and fastening terminal end 5 on the inner surface 3b.

Figure 2:
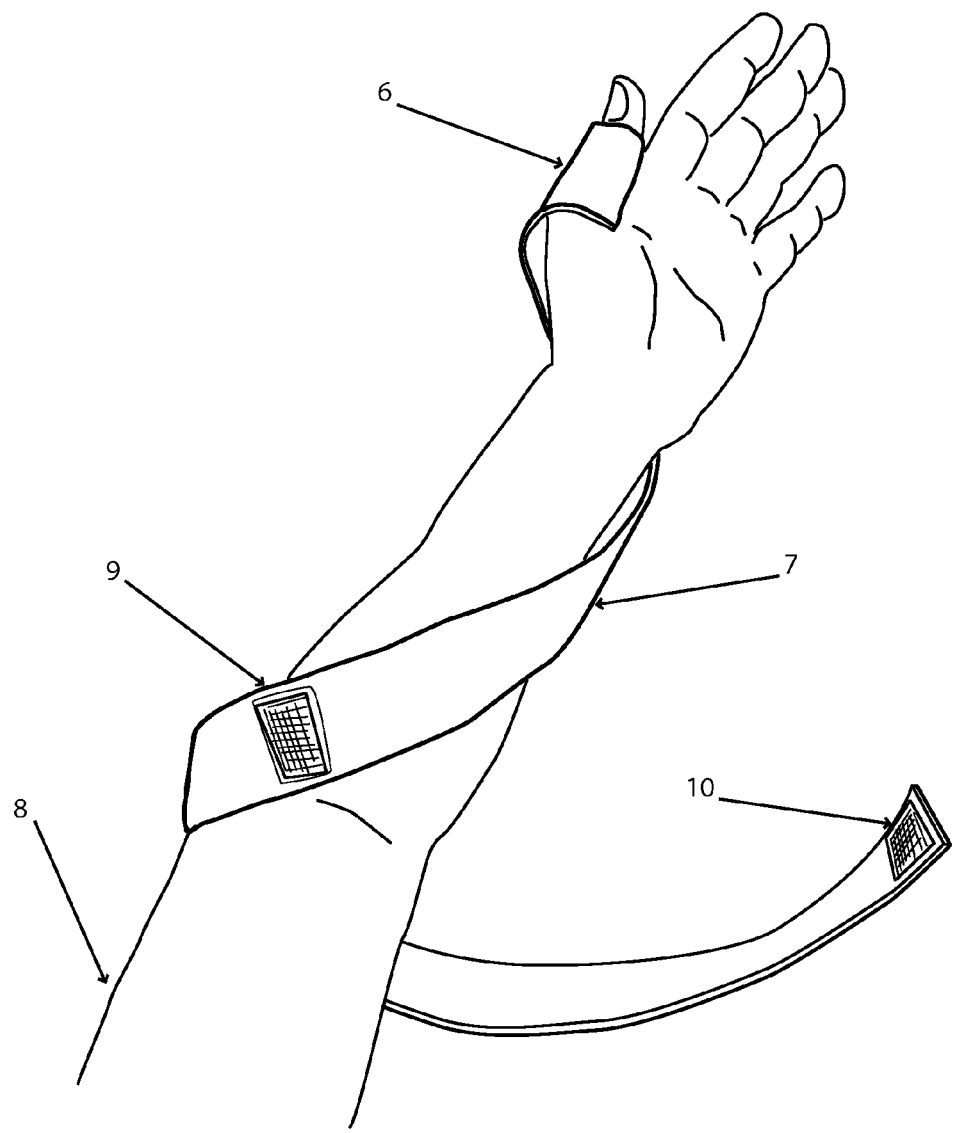
FIG. 2 is a perspective view of the arm brace of FIG. 1 loosely placed around an arm.

FIG. 2 shows the brace placed loosely on the user's arm. The notched double loop 6 end is placed on the thumb, the tension band portion 7 is wrapped around the forearm in a spiral fashion towards the elbow, then wrapped around to the distal portion of the upper arm 8. The supinating tension band section has a fastening material such as velcro on the outer surface 9. The corresponding velcro fastener on the inner surface of the terminal end of the brace 10 are shown unattached.

Figure 3:
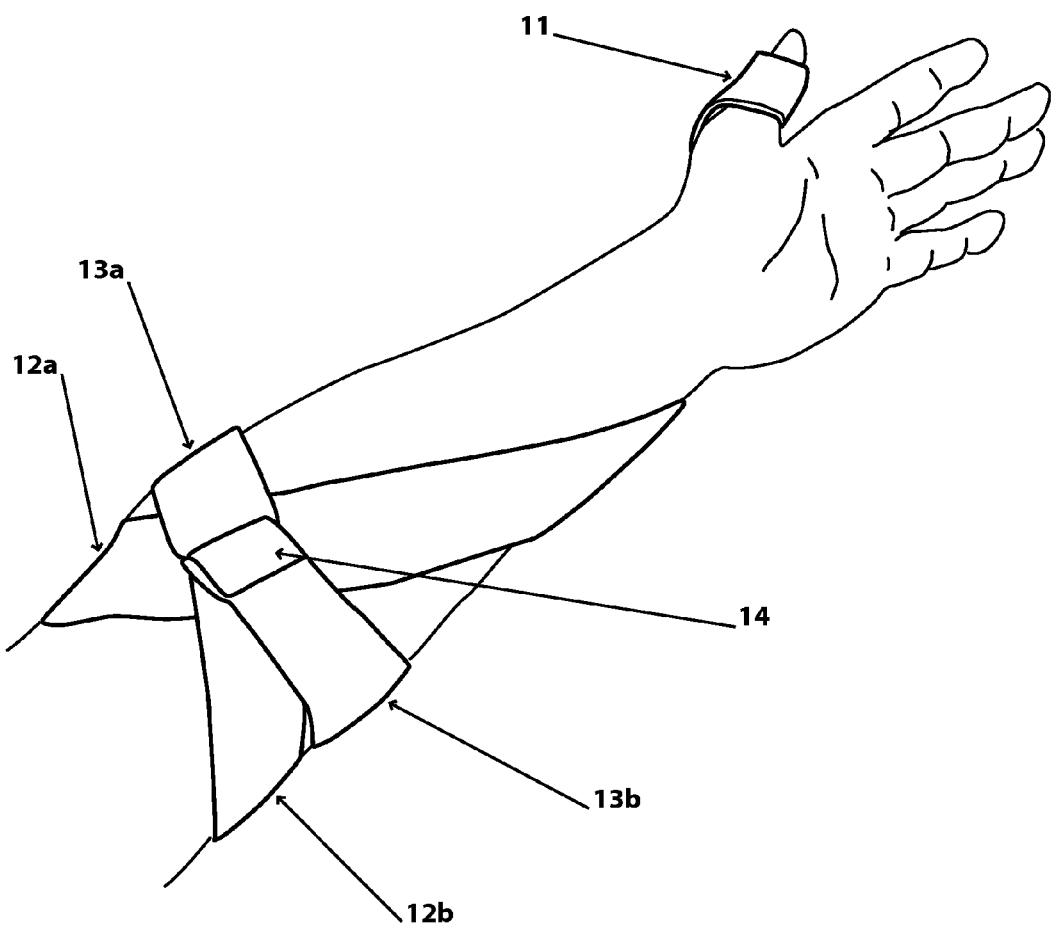
FIG. 3 is a perspective view of the arm brace of FIG. 1 wrapped around an arm.

FIG. 3 shows the supinating brace placed tightly on the arm. The notched double loop is secured tightly on the user's thumb 11, the tension band is wrapped tightly around the distal part of the upper arm above the elbow from lateral 12a to medial 12b, then wrapped over itself on the lateral posterior forearm 13a, to the medial anterior forearm 13b attaching with the velcro fastening attachments from the outer surface of the brace to the anchoring inner surface of the distal end of the brace 14.

Figure 4:
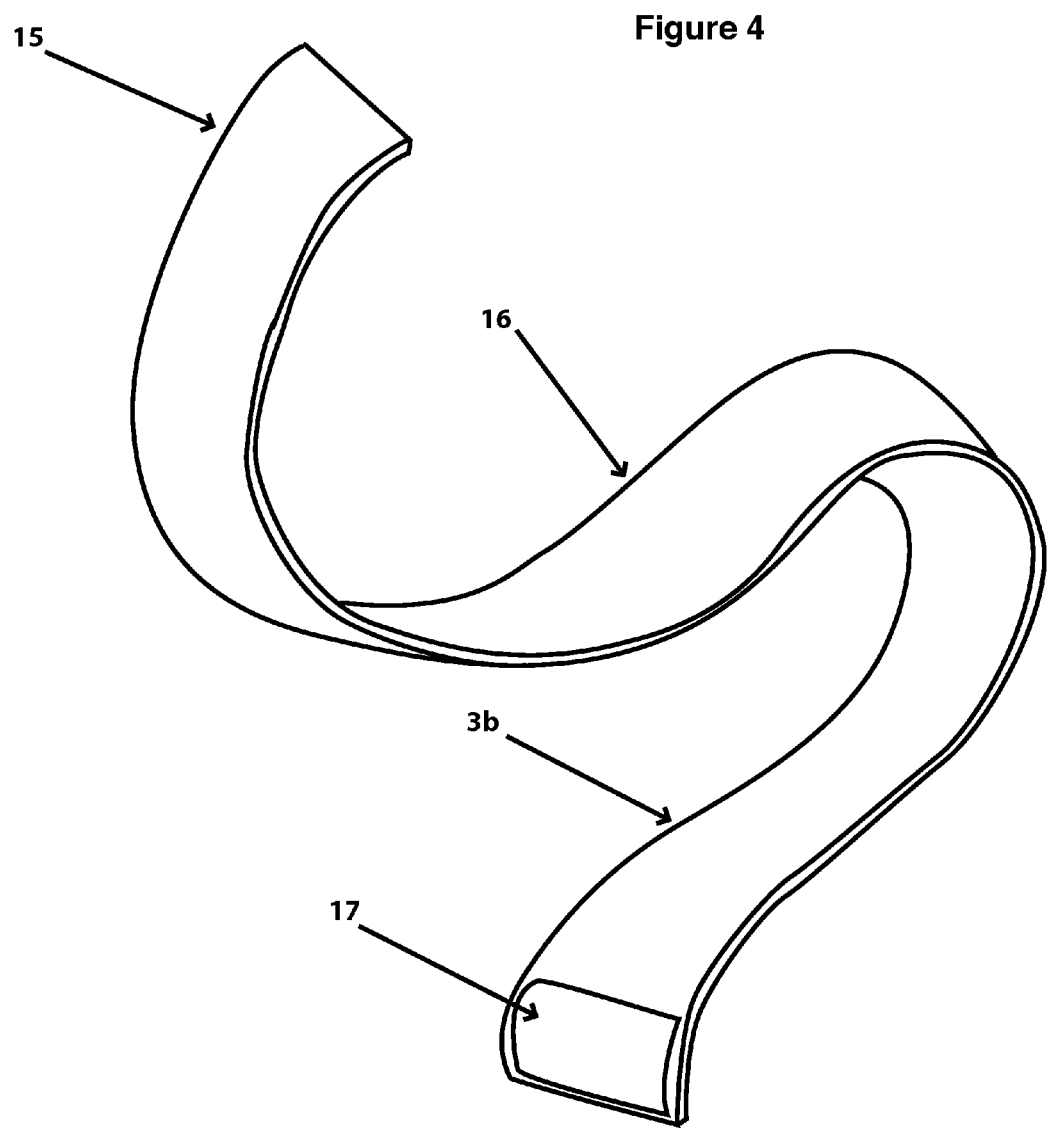
FIG. 4 is a perspective view of another embodiment of the arm brace of FIG. 1.

FIG. 4 shows a supinating arm brace device configuration with distal end containing a fastening attachment on the outer surface 15, elastic supinating tension band portion 16, and proximal end 16 containing fastening attachment 17 on the inner surface 18.

Figure 5:
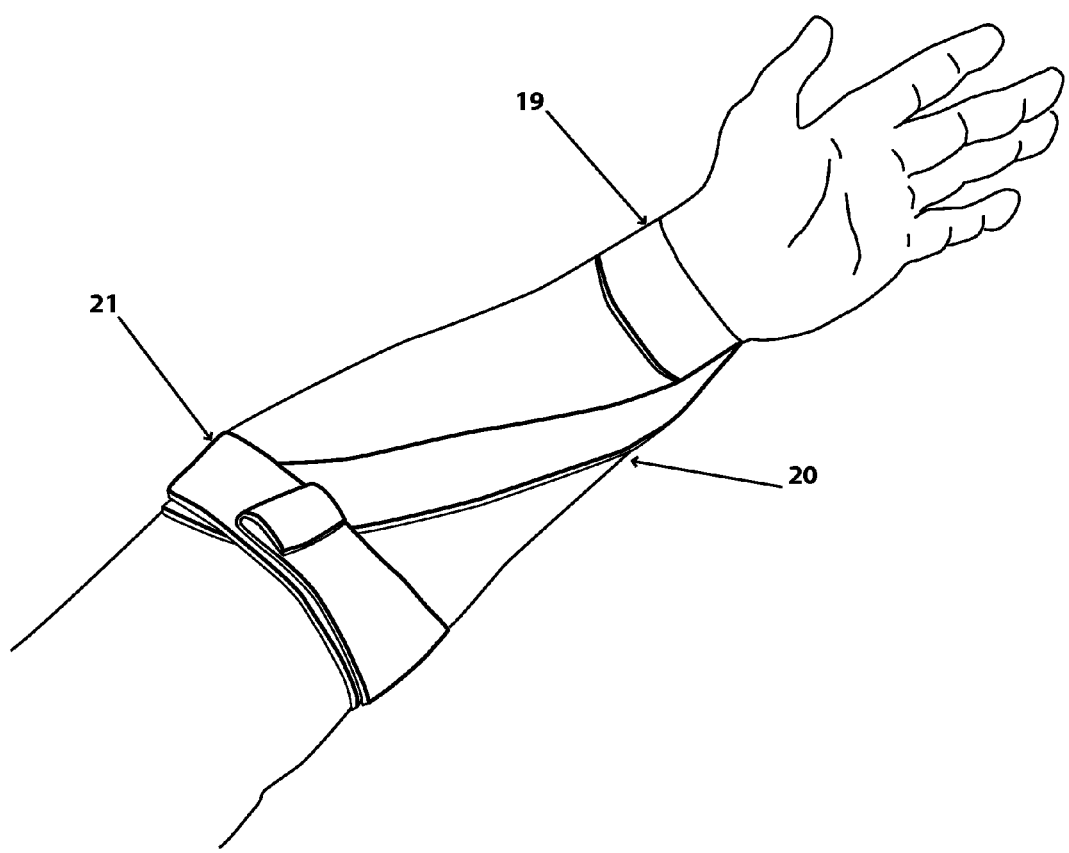
FIG. 5 is a perspective view of the arm brace of FIG. 4 wrapped around an arm.

FIG. 5 shows one configuration comprising of a supinating arm brace with distal fastening wrist cuff 19, with attached elastic supinating tension band portion with outer surface 20, and proximal arm cuff 21.

What is claimed is:

1. An arm brace for rehabilitating an arm of a person, the arm brace comprising:
    a band for wrapping around an arm, the band having a distal end and a proximal end;
    a looped section at the distal end of the band for accommodating a portion of a hand/wrist of the arm to anchor the band thereto;
    wherein the band is extendable to an extended position, such that the band exerts a force that causes supination of the arm when the looped section is anchored to the hand/wrist; and
    a fastener at the proximal end of the band for securing the proximal end of the band to another portion of the band when the band is in the extended position;
    wherein the looped section of the band has a loop that closes at a notched section of the band, such that the looped portion has angled openings for accommodating a digit of the hand.

2. The arm brace of claim 1, wherein the band is elastic.

3. The arm brace of claim 1, wherein the fastener releasably attaches the proximal end to the band.

4. The arm brace of claim 3, wherein:
    the band comprises an inner surface for contacting the arm and an outer surface; and
    the fastener comprises a hook and loop fastener, wherein the inner surface of the proximal end of the band fastens to the outer surface of the band.

5. The arm brace of claim 1, wherein the looped section is a fixed loop.

6. The arm brace of claim 1, wherein:
    the distal end of the band includes a second fastener; and
    the looped section at the distal end of the band is formed by a portion of the band secured to itself via the second fastener.

7. The arm brace of claim 6, wherein the second fastener releasably attaches the distal end to the band.

8. The arm brace of claim 7, wherein:
    the band comprises an inner surface for contacting the arm and an outer surface; and
    the fastener comprises a hook and loop fastener, wherein the outer surface of the proximal end of the band fastens to the inner surface of the band.

9. A method of rehabilitating an arm of a person with an arm brace, the method comprising:

anchoring an extendable band to an arm by positioning a portion of a hand/wrist of the arm in a looped section located at the distal end of the band;

extending the band around the arm such that it exerts a force that causes supination of the arm; and fastening a proximal end of the band to another portion of the band to secure the band in an extended position.

10. The method of claim 9, wherein the band is elastic.

11. The method of claim 9, wherein the step of fastening the proximal end of the band to another portion of the band comprises fastening the inner surface of the proximal end of the band to the outer surface of the band.

12. The method of claim 9, wherein the step of anchoring comprises wrapping a distal section of the band around a wrist and fastening the distal end to the band to form the looped section.

13. The method of claim 12, wherein the step of extending the band around the arm comprises:

wrapping the band at least partially around a forearm in a spiral direction;

pulling a proximal end of the strap to a lateral side of an elbow;

pulling the proximal end past the elbow and around an upper arm; and pulling the proximal end back towards the forearm.

14. The method of claim 9, wherein the step of anchoring comprises inserting at least one digit of a hand into a fixed loop.

15. The method of claim 14, wherein the step of extending the band around the arm comprises:

passing the band over the back of the hand; and wrapping the band at least partially around a wrist and forearm in a spiral direction;

pulling the proximal end of the band to a lateral side of the elbow;

pulling the proximal end past the elbow and around an upper arm; and pulling the proximal end back towards the forearm.

16. The method of claim 14, wherein the looped section of the band has a loop that closes at a notched section of the band, such that the looped portion has angled openings for accommodating the digit of the hand.

17. The method of claim 9, wherein the step of anchoring comprises inserting a thumb into a fixed loop.

18. The method of claim 9, further comprising the step of increasing the force exerted on the arm by stretching the band to increase the length of the band.

19. The method of claim 9, further comprising the step of decreasing the force exerted on the arm by relaxing the band to decrease the length of the band.

* * * * *